United States Patent
McClure et al.

(10) Patent No.: US 10,625,078 B2
(45) Date of Patent: *Apr. 21, 2020

(54) VISUAL PROSTHETIC APPARATUS FOR RETINAL STIMULATION

(71) Applicant: Second Sight Medical Products, Inc., San Fernando, CA (US)

(72) Inventors: Kelly H. McClure, Simi Valley, CA (US); Richard A. Castro, Rehovot (IL); Sanjay Gaikwad, Valencia, CA (US); Da-Yu Chang, Rowland Heights, CA (US); Scott M. Loftin, Rosamond, CA (US); Rongqing Dai, Valencia, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,101

(22) Filed: Aug. 3, 2015

(65) Prior Publication Data

US 2015/0335892 A1    Nov. 26, 2015

Related U.S. Application Data

(62) Division of application No. 11/893,260, filed on Aug. 15, 2007, now Pat. No. 9,095,709.

(51) Int. Cl.
*A61N 1/36*  (2006.01)
*A61N 1/05*  (2006.01)

(52) U.S. Cl.
CPC ........ *A61N 1/36046* (2013.01); *A61N 1/0543* (2013.01)

(58) Field of Classification Search
CPC .................................................. A61N 1/36046
See application file for complete search history.

(56) References Cited

U.S. PATENT DOCUMENTS

| | | |
|---|---|---|
| 5,109,844 A | 5/1992 | de Juan, Jr. et al. |
| 5,935,155 A | 8/1999 | Humayan et al. |
| 5,944,734 A | 8/1999 | Greenberg et al. |
| 6,400,989 B1 | 6/2002 | Eckmiller |
| 6,458,157 B1 | 10/2002 | Suaning |
| 6,718,209 B2 | 4/2004 | Williamson et al. |
| 6,974,533 B2 | 12/2005 | Zhou |
| 7,260,435 B2 * | 8/2007 | Ibrahim ............. A61N 1/36032 607/57 |

(Continued)

FOREIGN PATENT DOCUMENTS

WO    WO 03/076012    9/2003

*Primary Examiner* — Carl H Layno
*Assistant Examiner* — Jennifer L Ghand
(74) *Attorney, Agent, or Firm* — Scott Dunbar

(57) ABSTRACT

A visor for visual stimulation of visually impaired subjects is shown. The visor comprises a frame, a coil, a camera and a mounting system. A connector allows the coil to be positioned along a first direction. A sliding device allows the coil to be positioned along a second direction. Positioning of the visor on a subject's nose allows the coil to be positioned along a third direction. Positioning of the coil along the first, second or third direction is useful to maximize coupling RF coupling between the coil and an internal coil implanted on a subject wearing the visor.

8 Claims, 11 Drawing Sheets

(56) References Cited

U.S. PATENT DOCUMENTS

| | | | |
|---|---|---|---|
| 8,498,713 B2* | 7/2013 | McClure | A61N 1/36046 607/116 |
| 2002/0019669 A1* | 2/2002 | Berrang | A61N 1/36036 623/10 |
| 2005/0159791 A1* | 7/2005 | Daly | H04R 25/606 607/57 |
| 2005/0201585 A1 | 9/2005 | Jannard et al. | |
| 2005/0222624 A1 | 10/2005 | Greenberg et al. | |
| 2006/0129207 A1 | 6/2006 | Fried et al. | |
| 2007/0191673 A1* | 8/2007 | Ball | H04R 25/606 600/25 |
| 2008/0027510 A1* | 1/2008 | McClure | A61N 1/3787 607/54 |

* cited by examiner

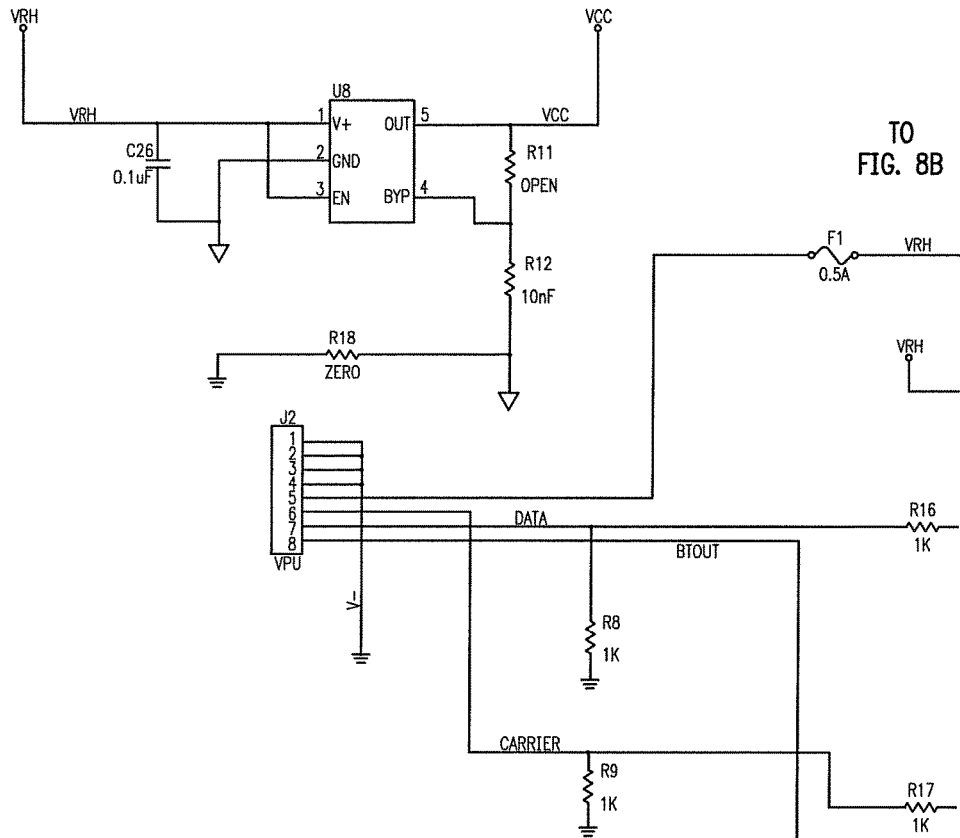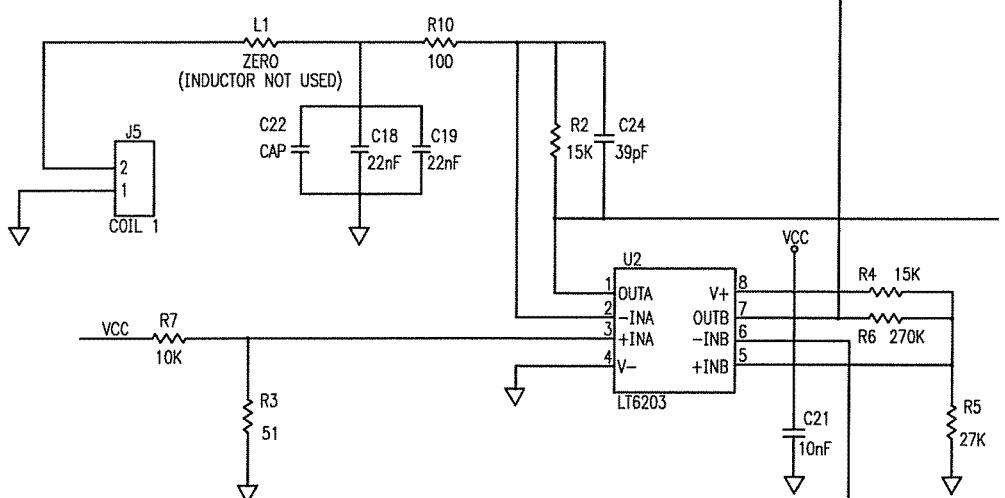
FIG. 8A

BILL OF MATERIALS

| ITEM NO. | SECOND SIGHT PART NUMBER | TITLE | QUANTITY | NOTES |
|---|---|---|---|---|
| 1 | 101055-000 | PCB, RF Board, A60 Human Trial | 1 | Assembly drawing contains Layout file |
| 2 | 100966-005 | Capacitor, 0.1uF, 50V, 0603, X7R | 7 | C1,C2,C3,C4,C5,C6,C26 |
| 3 | 100965-004 | Capacitor, 1uF, 15V, 0603, X5R | 1 | C7 |
| 4 | 100964-025 | Capacitor, 100pF, 50V, 0603, COG | 1 | C8 |
| 5 | 100964-031 | Capacitor, 180pF, 50V, 0603, COG | 1 | C9 |
| 6 | 100964-001 | Capacitor, 10pF, 50V, 0603, COG | 1 | C10 |
| 7 | 100978-002 | Capacitor, 3.3uF, 16V, 805, X5R | 2 | C11,C12 |
| 8 | 100964-021 | Capacitor, 68pF, 50V, 0603, COG | 1 | C13 |
| 9 | 100964-045 | Capacitor, 680pF, 50V, 0603, COG | 1 | C14 |
| 10 | 100966-002 | Capacitor, 10nF, 50V, 0603, X7R | 4 | C15,C20,C21,R12* |
| 11 | 100961-030 | Capacitor, 22000pF, 50V, 0605, COG | 2 | C18,C19 |
| 12 | 100967-002 | Capacitor, 6-30pF Trimmer, SMT | 1 | C23 |
| 13 | 100964-015 | Capacitor, 39pF, 50V, 0603, COG | 1 | C24 |
| 14 | 100961-TAB | Capacitor, 50V, 0805, COG | 0 | C22, Value determined after manufacturing test |
| 15 | 100961-033 | Capacitor, 12000pF, 50V, 0805, COG | 1 | C25 |
| 16 | 100967-001 | Capacitor, 3-10pF Trimmer, SMT | 1 | C27 |
| 17 | 100979-017 | Coil, 680uH, Molded, Unshielded | 1 | L4 |
| 18 | 100990-000 | Hand Wound Inductor, 280-300nH | 1 | L5 |
| 19 | 100975-152 | Resistor, 1.5K, 0603, 5%, 1/10Watt | 1 | R1 |
| 20 | 100975-153 | Resistor, 15K, 0603, 5%, 1/10Watt | 2 | R2,R4 |
| 21 | 100975-510 | Resistor, 51, 0603, 5%, 1/10Watt | 1 | R3 |
| 22 | 100975-273 | Resistor, 27K, 0603, 5%, 1/10Watt | 1 | R5 |
| 23 | 100975-274 | Resistor, 270K, 0603, 5%, 1/10Watt | 1 | R6 |
| 24 | 100975-103 | Resistor, 10K, 0603, 5%, 1/10Watt | 1 | R7 |
| 25 | 100975-102 | Resistor, 1K, 0603, 5%, 1/10Watt | 4 | R8,R9,R16,R17 |
| 26 | 100975-101 | Resistor, 100, 0603, 5%, 1/10Watt | 1 | R10 |
| 27 | 100975-473 | Resistor, 47K, 0603, 5%, 1/10Watt | 1 | R14 |
| 28 | 100975-471 | Resistor, 470, 0603, 5%, 1/10Watt | 1 | R15 |
| 29 | 100975-000 | Resistor, zero, 0603, 5%, 1/10Watt | 2 | R18,L1 |
| 30 | 100981-002 | Fuse, 0.5 Amp, 0603, Fast Acting | 1 | F1 |
| 31 | 100980-001 | Connector, 8 pos., 1.25mm header | 0 | J2 Do not install |
| 32 | 100982-001 | Diode, SOT-23, MMBD914 | 1 | D2 |
| 33 | 100983-001 | IC, FM IF System, 16-SOIC, SA604 | 1 | U1 |
| 34 | 100964-001 | IC, Operational Amplifier, 8-SOIC, LT6203 | 1 | U2 |
| 35 | 100965-001 | IC, Pin Driver, 8-SO, EL71581 | 2 | U3,U4 |
| 36 | 100986-001 | Ceramic Filter, CFXD450KCFA, SMT | 2 | U6,U7 |
| 37 | 100987-003 | IC, LDO Regulator, LP2985AIM5-4.8, SOT-23-5 | 1 | U8 |
| 38 | 100957-001 | Solder | A/R | Active Core Solder |
| 39 | 100957-002 | Solder | A/R | Rosin Core Solder |
| 40 | 130156-010 | Loctite 495 Instant Adhesive Sealant | A/R | Superglue |

FIG. 9

VISUAL PROSTHETIC APPARATUS FOR RETINAL STIMULATION

CROSS REFERENCE TO RELATED APPLICATIONS

This application is a divisional application of, and claims priority to, U.S. application Ser. No. 11/893,260, filed Aug. 15, 2007, now U.S. Pat. No. 9,095,709, for Visual Prosthetic Apparatus for Retinal Simulation, which claims priority to U.S. Provisional Ser. 60/876,645 for "Visor for a Visual Prosthesis" filed on Dec. 22, 2006 and to PCT application No. PCT/US2007/013918 for "Apparatus and Method for Electrical Stimulation of Human Retina" filed on Jun. 15, 2007, both of which are incorporated herein by reference in their entirety.

GOVERNMENT RIGHTS NOTICE

This invention was made with government support under grant No. R24EY12893-01, awarded by the National Institutes of Health. The government has certain rights in the invention.

FIELD

The present disclosure is generally directed to neural stimulation and more specifically to a visual prosthetic apparatus for retinal stimulation.

BACKGROUND

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., de Juan, et al., 99 Am. J. Ophthalmol. 272 (1985). These retinal tacks have proved to be biocompatible and remain embedded in the retina, with the choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY

According to a first embodiment of the present disclosure, a visual prosthetic apparatus for retinal stimulation is disclosed, comprising: an implantable portion and an external portion, wherein the implantable portion comprises an RF receiver, an internal coil, and an array of electrodes, wherein the external portion comprises a frame, a camera mounted on the frame and an external coil mounted on the frame, and wherein distance between the internal coil and the external coil is controllable along at least one of a medial-lateral direction, anterior-posterior direction and a superior-inferior direction.

According to a second embodiment of the present disclosure, a visor for visually impaired subjects is disclosed, comprising: a frame; a coil arrangement including an external coil; a camera; a mounting system to mount the coil arrangement on the frame; a connection between the camera and the mounting system; a flexible connector connecting the coil arrangement with the mounting system, the flexible connector being adapted to adjust positioning of the external coil along a first direction; a sliding device positioned between the frame and the mounting system, the sliding device being adapted to adjust positioning of the external coil along a second direction; and a structure attached to the frame, the structure allowing positioning of the visor on a subject's nose, wherein movement of the visor on the subject's nose allows positioning of the external coil along a third direction.

Further embodiments are disclosed throughout the specification, drawings and claims of the present disclosure.

BRIEF DESCRIPTION OF THE DRAWINGS

FIGS. 8A and 8B (to be viewed side by side) show a circuital diagram of RF circuitry 17 shown in FIG. 4.

FIG. 9 shows a table with exemplary values for the components of the circuit of FIGS. 8A and 8B.

DETAILED DESCRIPTION

Figure 1:
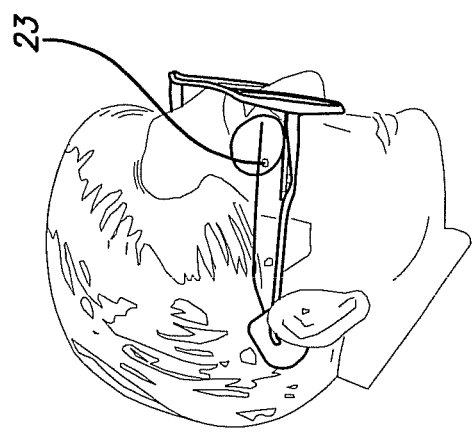
FIG. 1 is a brief schematic view of an implanted visual prosthesis.

FIG. 1 is a schematic view of prosthesis for stimulating retinal cells. Patients suffering from retinitis pigmentosa (RP) sustain severe vision loss as a result of photoreceptor death. In the preferred prosthesis, the electrode array is aligned in a 6×10 matrix with the wider dimension oriented to horizontal in the visual field, implanted epiretinally, which covers about 10×20 degrees of visual angle. The upper sub figure shows a schematic of an electrode array in a 6×10 configuration. The subfigure from this schematic details a graphic representation of the system of neural cells under each electrode, wherein the neural cells shown are no longer organized, but unorganized with significant cell death.

Figure 2:
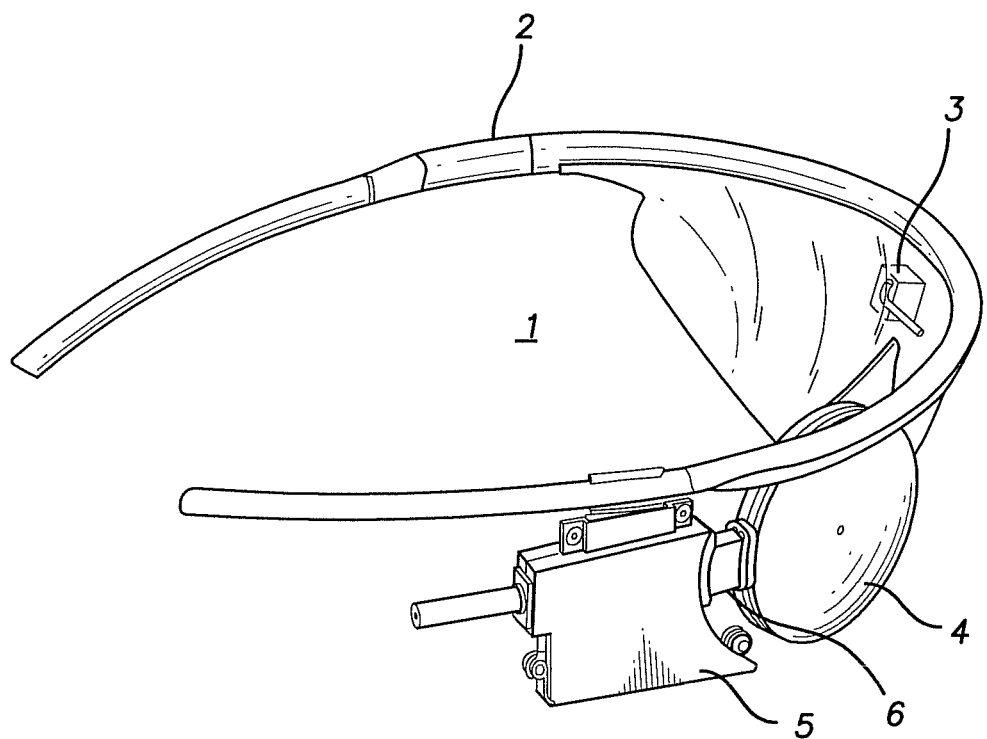
FIGS. 2 and 3 show perspective views of an external portion of a visual prosthetic apparatus.
Figure 3:
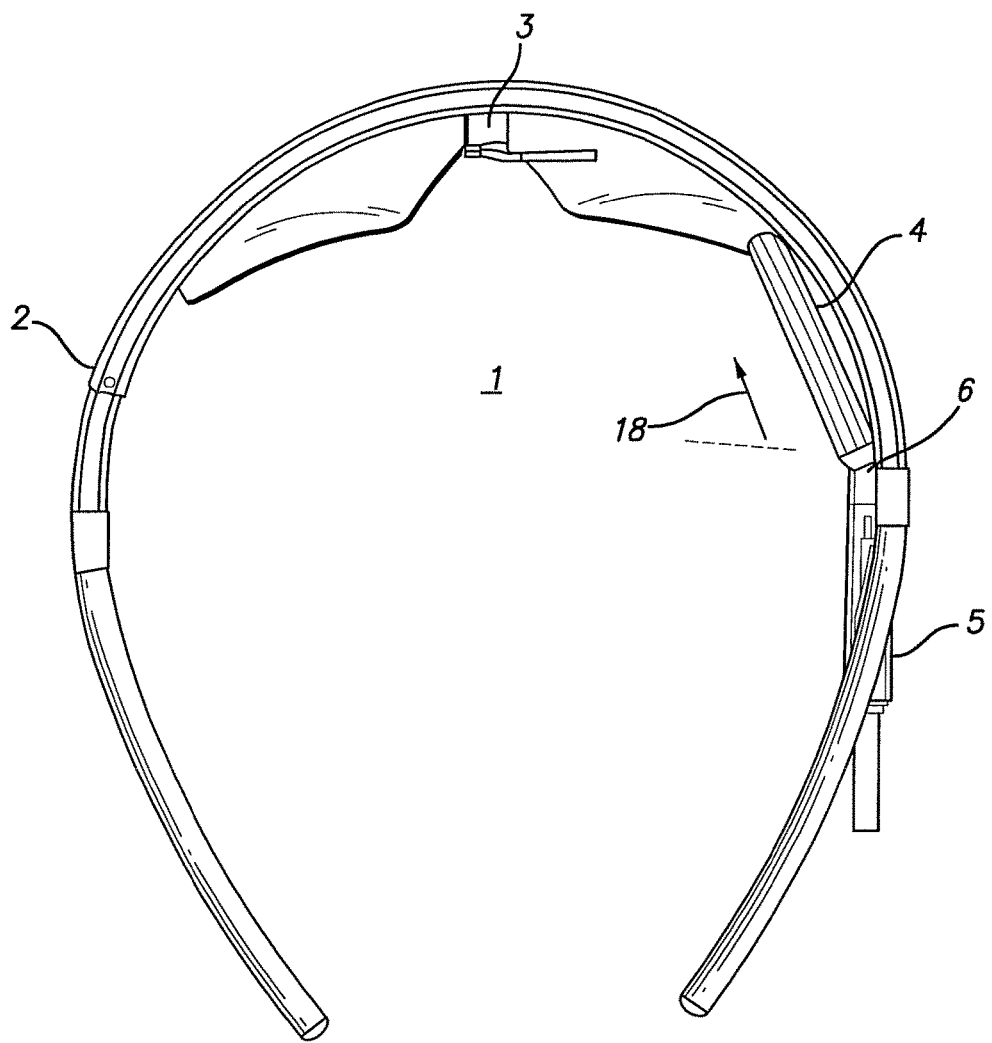

FIGS. 2 and 3 show two different perspective views of an external portion of a visual prosthetic apparatus according to the present disclosure. 'External' is here meant to indicate that the portion is external to the human body, and not implanted therein. External portion 1 is adapted to be used in combination with an implantable portion 23, shown in FIGS. 6 and 7. Turning to FIGS. 2 and 3, the external portion 1 comprises a frame 2 holding a camera 3, an external coil arrangement 4 and a mounting system 5 for the external coil arrangement 4. The external coil arrangement 4 comprises external transmitting and receiving radio-frequency (RF) coils (later shown in FIG. 4) adapted to be used together and communicate with an internal RF coil (later shown in FIGS. 6 and 7). The mounting system 5 also encloses the RF circuitry 17 (see FIG. 4) for modulating, demodulating, transmitting, and receiving an RF signal. External coil arrangement 4 and mounting system 5 are connected by a flexible connector 6.

Figure 4:
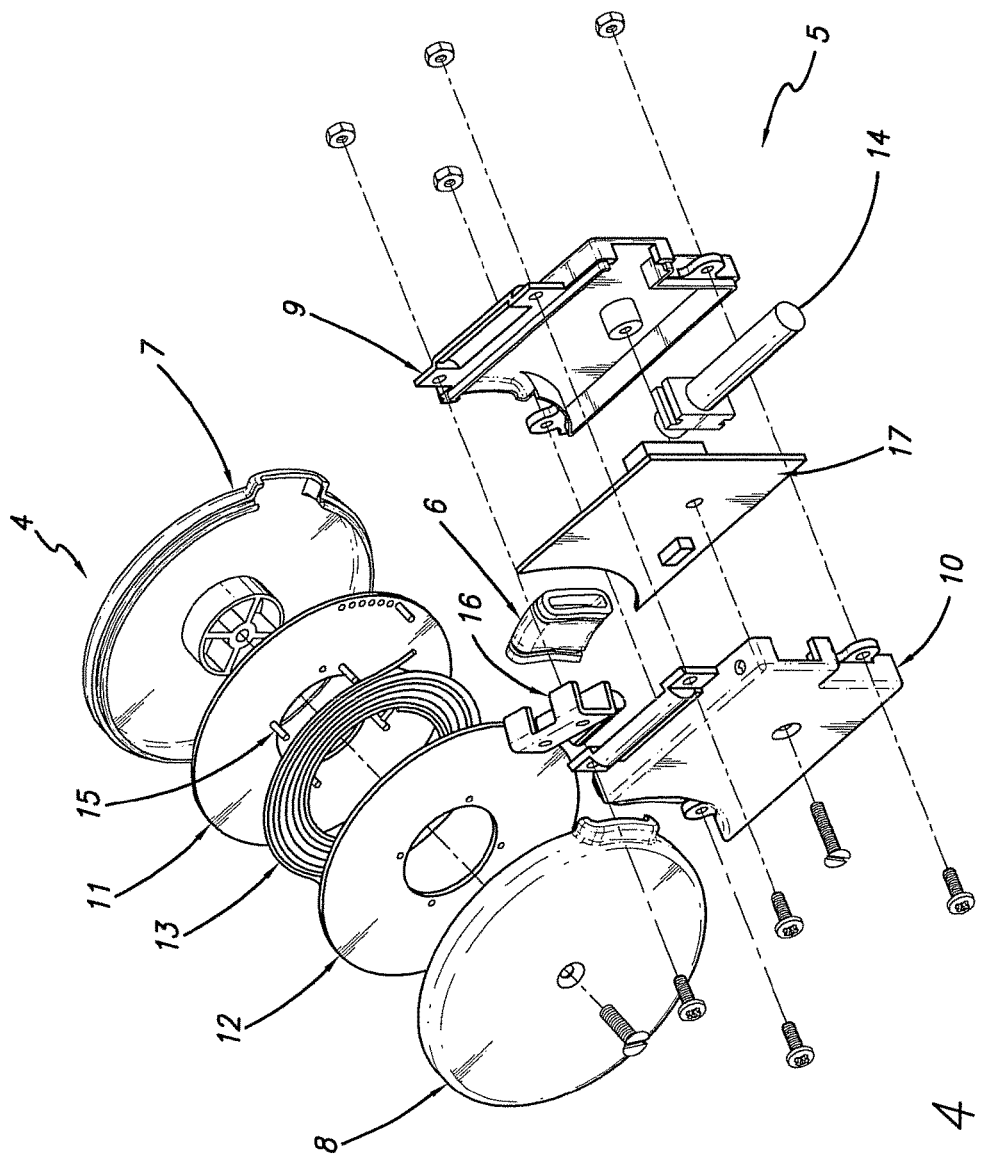
FIG. 4 is an exploded view of the external coil arrangement and mounting system shown in FIGS. 2 and 3.
Figure 8B:
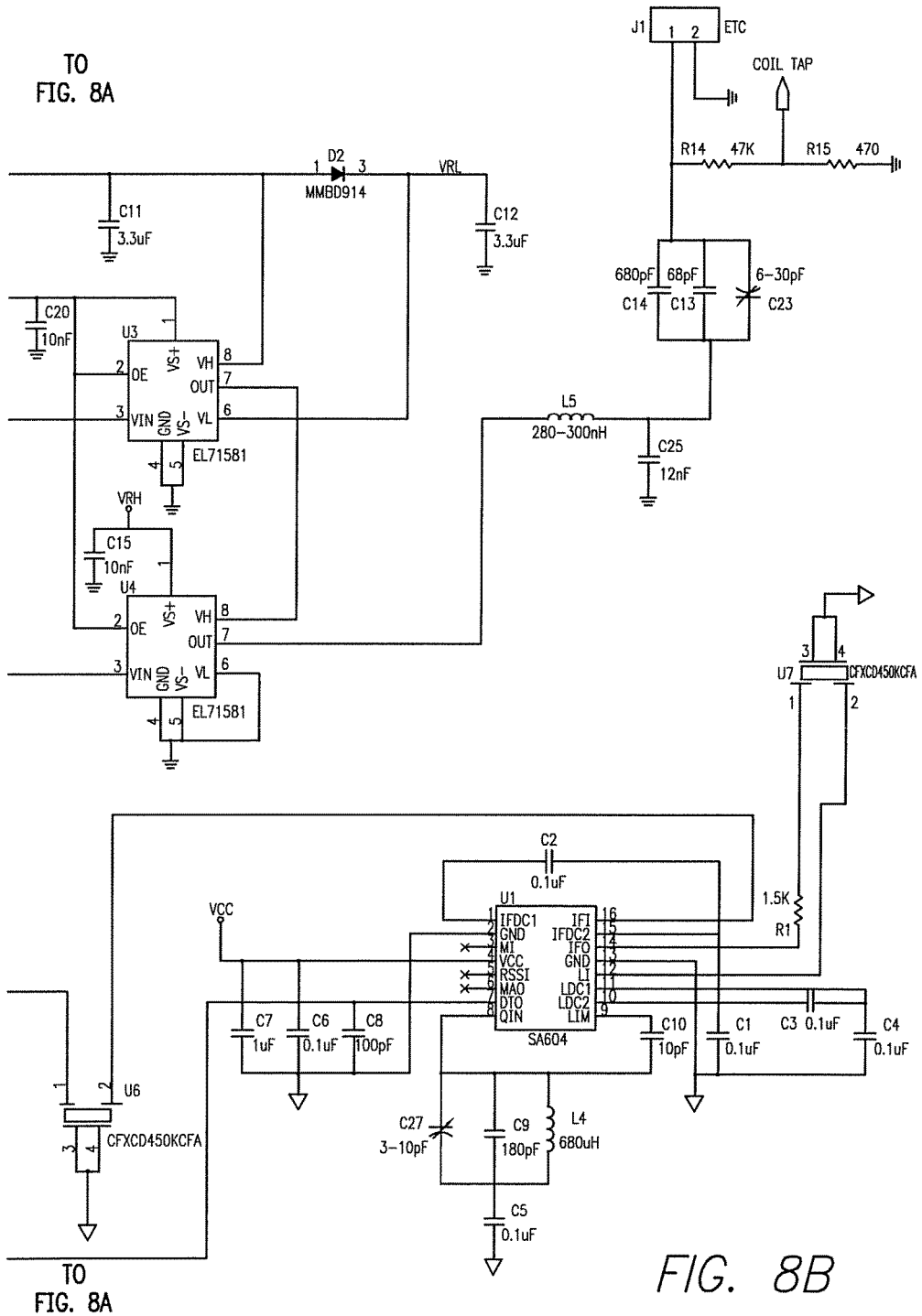
Figure 10:
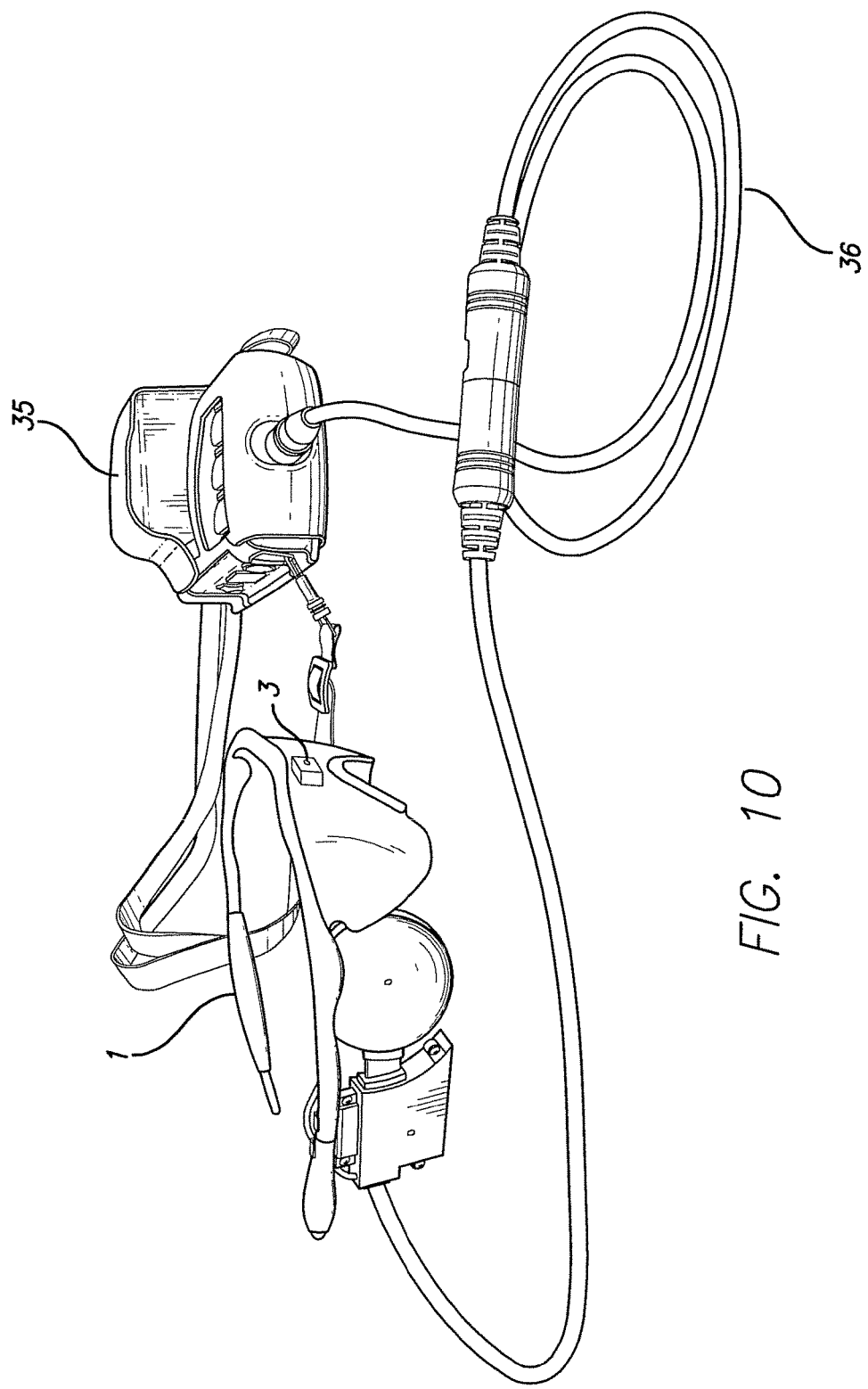
FIG. 10 shows an arrangement comprising a visor, a visual processing unit and a cable connecting the visor to the visual processing unit.

FIG. 4 shows an exploded view of the external coil arrangement 4 and mounting system 5. As also shown in FIGS. 2 and 3, the external coil arrangement 4 and mounting system 5 are connected by a flexible connector 6. In particular, the flexible connector 6 is attached to RF coil enclosure halves 7 and 8 on the coil side and to enclosure case halves 9 and 10 on the mounting system side. The external coil arrangement 4 comprises coil enclosure halves 7 and 8, enclosing printed circuit boards (PCB) 11 and 12 surrounding an RF transmitting coil 13. The PCBs 11 and 12 further include telemetry receiving coils. The mounting system 5 comprises case halves 9 and 10 enclosing an RF visor cable assembly 14. Other mechanical components shown in FIG. 4 include: wires 15 connecting PCBs 11 and 12; a mounting bracket 16 (later described in FIG. 5); and RF circuitry 17 located between case halves 9 and 10. While video image processing is done in a remote video processing unit (shown in FIG. 10), the RF circuitry 17 is incorporated into the mounting system 5 to reduce losses in the cable connecting the video processing unit to the glasses. PCBs 11 and 12 can be made of glass base epoxy and laminated with copper. An exemplary circuital diagram of RF circuitry 17 is shown in FIGS. 8A, 8B and 9. FIG. 10 shows an arrangement comprising a visor 1 connected to a visual processing unit 35 through a cable 36.

Figure 6:
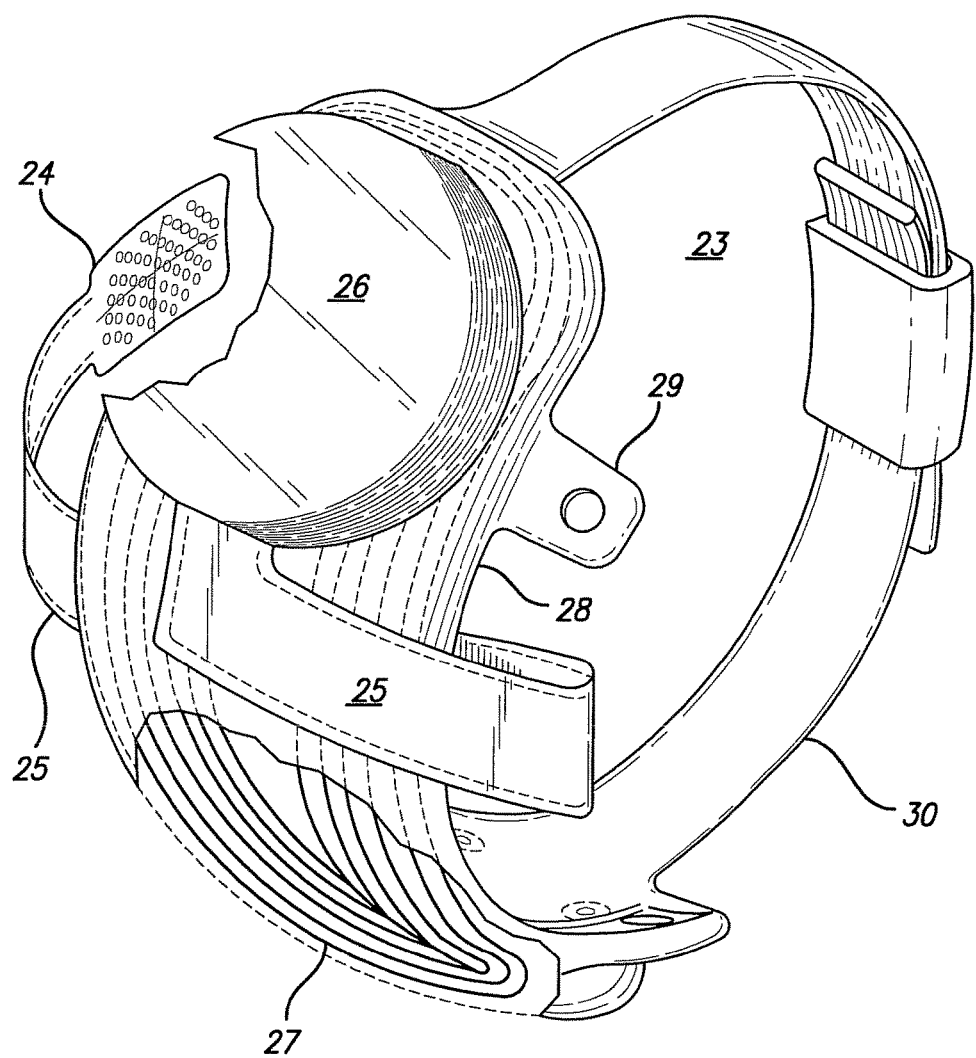
FIG. 6 shows a perspective view of the implantable portion of the visual prosthesis.
Figure 7:
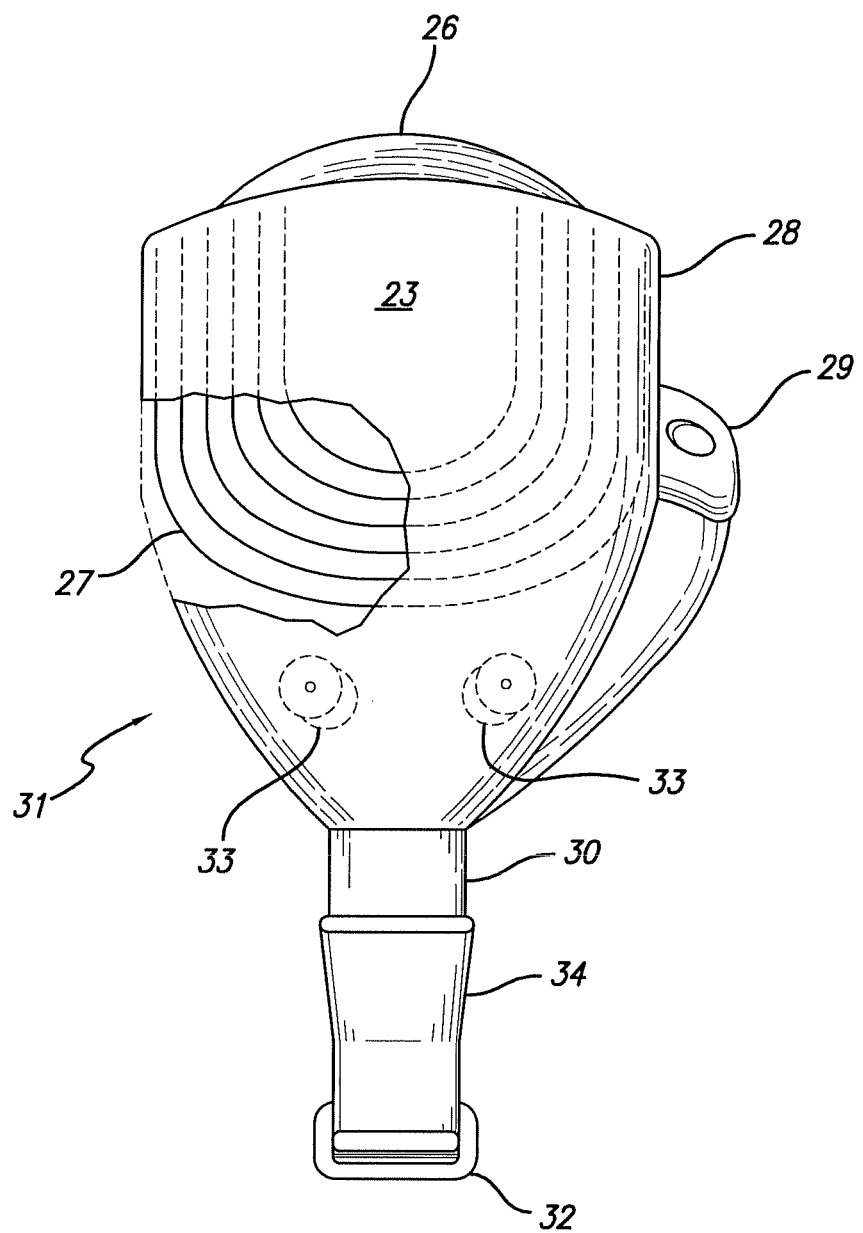
FIG. 7 is a side view of the implantable portion of the visual prosthesis.

Three structural features are provided in the visual prosthesis to control the distance, and thereby reduce the distance, between the external coil 13 (included in arrangement 14) and the inductive (implanted) coil (27, FIGS. 6 and 7). The three structural features correspond to movement of the external coil along the three possible spatial axes occupied by the two coils. That is, the external and inductive coils can be viewed as being separated in anatomical axes: the medial-lateral, superior-inferior, and the anterior-posterior axis. Control of the distance between external coil 13 and implanted coil 27 is important, because it allows a better signal transmission via the 13-27 inductive coupling.

The first structural feature is adapted to reduce the distance between the coils along the medial-lateral axis by bending the external coil arrangement 4, thus bending the external coil 13. The distance in this medial-lateral axis should be equivalent to the separation distance of the coils if the centers of the coils are aligned. The enclosure 4 of the external coil 13 is attached to the mounting system 5, which is attached to the leg frame 2 of the visual apparatus. While the RF circuitry within the mounting system 5 is in line with the leg frame 2, the external coil 13 has been given a preferential bend 18 towards the face using the flexible connector 6 shown in FIG. 4. With the external coil 4, 13 angled toward the face (e.g., at 25 degrees) (see FIGS. 2 and 3), the external coil 4, 13 makes contact with the subject's face and the flexible connector allows conformation to the subject's facial contours. Thus, the external coil 4, 13 is brought in as close as possible in the medial-lateral axis for the subject.

The second structural feature is a sliding bar mechanism adapted to control movement of the external coil 4, 13 along the anterior-posterior axis. The point at which the mounting system 5 connects to the visor allows for adjustment along this anterior-posterior axis (e.g., a 7 mm adjustment). The sliding bar mechanism can be fixed in place when the optimal position is found by tightening two screws on the sides of the sliding bar.

Figure 5:
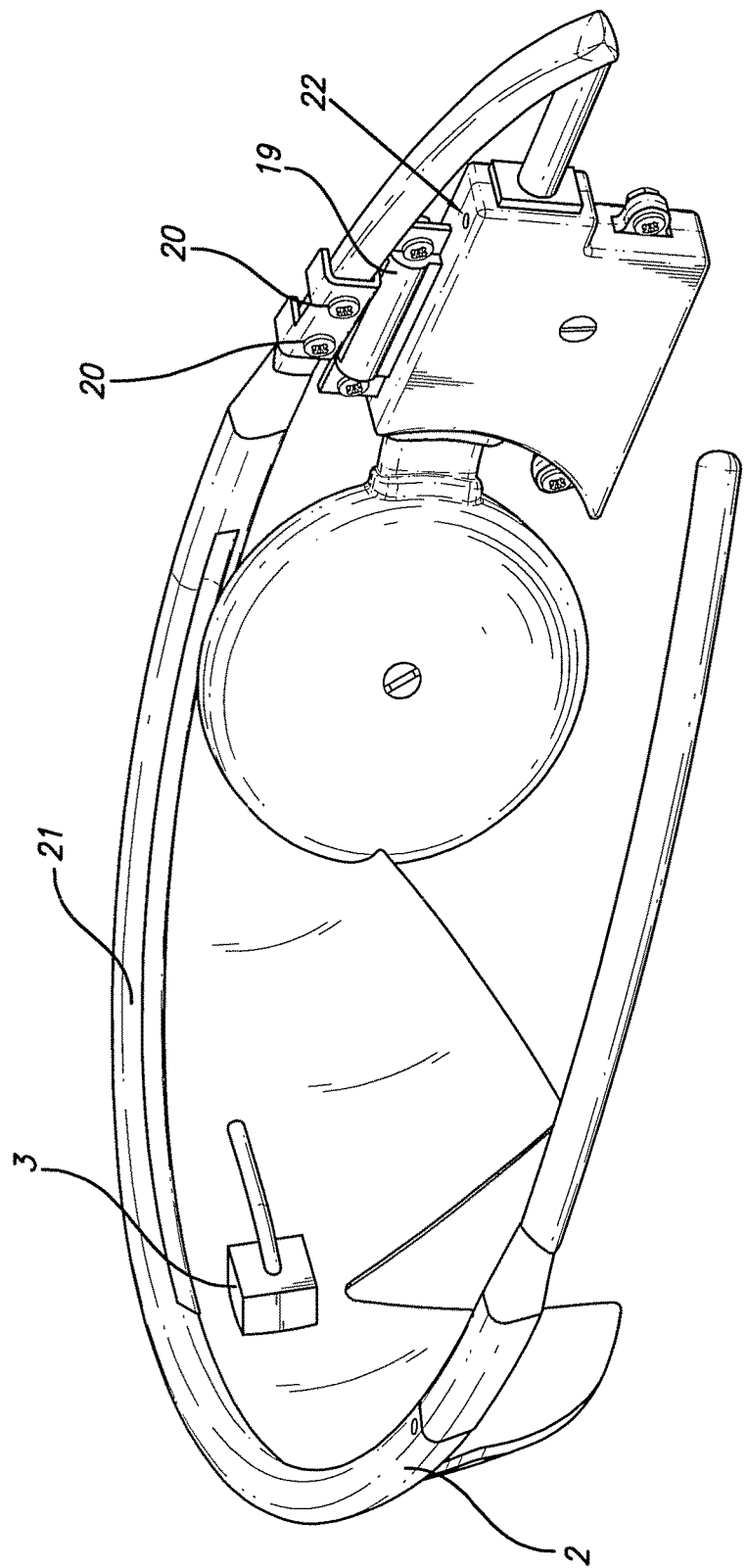
FIG. 5 is a further perspective view of the external portion of the visual prosthetic apparatus.

In particular, reference can be made to FIG. 5, which shows a further perspective view of the apparatus shown in FIGS. 2 and 3. In particular, FIG. 5 shows a sliding bar mechanism 19 which is tightened into position by screws 20. FIG. 5 also shows a trench 21 for routing camera cable connected to the camera 3. The camera cable end can be inserted into hole 22 of the mounting system 5.

The third structural feature is adjustment of the position of the external coil 4, 13 along the superior-inferior axis by varying the placement of the visual apparatus 1 along the subject's nose. When the visual apparatus 1 is worn close to the face, the external coil 13 is higher, and when worn further from the face, the external coil 13 is lower. Using these three structural adjustments alone or in combination, the coil separation distance can be adjusted to obtain an optimal RF link for individual subjects.

FIG. 6 shows a perspective view of an implantable portion 23 of a retinal prosthesis as disclosed. An electrode array 24 is mounted by a retinal tack or similar means to the epiretinal surface. The electrode array 24 is electrically coupled by a cable 25, which can pierce the sclera and be electrically coupled to an electronics package 26 external to the sclera. Electronic package 26 includes the RF receiver and electrode drivers.

The electronics package 26 can be electrically coupled to the secondary inductive coil 27. In one aspect, the secondary inductive coil 27 is made from wound wire. Alternatively, the secondary inductive coil may be made from a thin film polymer sandwich with wire traces deposited between layers of thin film polymer. The electronics package 26 and secondary inductive coil 27 are held together by a molded body 28. The molded body 28 may also include suture tabs 29. The molded body narrows to form a strap 30 which surrounds the sclera and holds the molded body 28, secondary inductive coil 27, and electronics package 26 in place. The molded body 28, suture tabs 29 and strap 30 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the secondary inductive coil 27 and molded body 28 are oval shaped, and in this way, a strap 30 can better support the oval shaped coil.

The entire implantable portion 23 is attached to and supported by the sclera of a subject. The eye moves constantly. The eye moves to scan a scene and also has a jitter motion to prevent image stabilization. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 7 shows a side view of the implantable portion of the retinal prosthesis, in particular, emphasizing the fan tail 31. When the retinal prosthesis is implanted, the strap 30 has to be passed under the eye muscles to surround the sclera. The secondary inductive coil 27 and molded body 28 should also follow the strap under the lateral rectus muscle on the side of the sclera. The implantable portion 23 of the retinal prosthesis is very delicate. It is easy to tear the molded body 28 or break wires in the secondary inductive coil 27. In order to allow the molded body 28 to slide smoothly under the lateral rectus muscle, the molded body is shaped in the form of a fan tail 31 on the end opposite the electronics package 26. Element 32 shows a retention sleeve, while elements 33 and 34 show holes for surgical positioning and a ramp for surgical positioning, respectively.

In summary, a visual prosthetic apparatus is provided. The apparatus provides a means for adjusting the RF link to the internal coils. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A visual prosthesis apparatus comprising:
   a frame, in the form of a pair of glasses;
   a camera mounted on the frame providing a video image
   an adjustable mounting system mounted on the frame;
   a coil mounted on the adjustable mounting system by a flexible connector to move the coil relative to the frame along a medial-lateral direction;
   the adjustable mounting system further including a slide to move the coil along the frame in an anterior-posterior direction, and to hold the coil fixed after adjustment;
   a visual processing unit processing the video image; and
   a cable connecting the frame with the visual processing unit, carrying the video image.

2. The apparatus of claim 1, wherein the slide is a sliding bar mechanism, the sliding bar mechanism connecting the adjustable mounting system to the frame, wherein movement of the adjustable mounting system with respect to the frame along the sliding bar mechanism allows adjustment of the coil along the anterior-posterior direction.

3. The apparatus of claim 1, further comprising radio frequency (RF) circuitry supported by the frame.

4. The apparatus of claim 1, wherein an RF circuit is mounted to the adjustable mounting system and the coil is mounted by the flexible connector to the adjustable mounting system and driven by the RF circuit.

5. The apparatus of claim 1, wherein the coil is positioned between two circuit boards.

6. The apparatus of claim 5, wherein at least one of the circuit boards includes a telemetry receiving coil.

7. The apparatus of claim 6, wherein both of the circuit boards include telemetry receiving coils.

8. The apparatus of claim 1, wherein the slide is a sliding bar mechanism and the adjustable mounting system is attached to the frame by the sliding bar mechanism including set screws to prevent sliding.

* * * * *